US009164037B2

(12) United States Patent
Bassler et al.

(10) Patent No.: US 9,164,037 B2
(45) Date of Patent: *Oct. 20, 2015

(54) METHOD AND SYSTEM FOR EVALUATION OF SIGNALS RECEIVED FROM SPATIALLY MODULATED EXCITATION AND EMISSION TO ACCURATELY DETERMINE PARTICLE POSITIONS AND DISTANCES

(75) Inventors: Michael Bassler, Menlo Park, CA (US); Peter Kiesel, Palo Alto, CA (US); Oliver Schmidt, Palo Alto, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 1439 days.

This patent is subject to a terminal disclaimer.

(21) Appl. No.: 11/698,338

(22) Filed: Jan. 26, 2007

(65) Prior Publication Data
US 2008/0183418 A1    Jul. 31, 2008

(51) Int. Cl.
| | | |
|---|---|---|
| *G01N 33/48* | (2006.01) | |
| *G01N 21/64* | (2006.01) | |
| *G06F 19/00* | (2011.01) | |
| *G06F 19/12* | (2011.01) | |
| G01N 31/00 | (2006.01) | |
| G06G 7/58 | (2006.01) | |
| G01N 15/10 | (2006.01) | |
| G01N 15/14 | (2006.01) | |

(52) U.S. Cl.
CPC ........ *G01N 21/6408* (2013.01); *G01N 21/6458* (2013.01); *G06F 19/12* (2013.01); *G06F 19/345* (2013.01); *G01N 2015/1075* (2013.01); *G01N 2015/1486* (2013.01); *G06F 2217/16* (2013.01)

(58) Field of Classification Search
CPC ............. G06F 19/3418; G06F 19/345; G06F 19/3462; G06F 2217/16
See application file for complete search history.

(56) References Cited

U.S. PATENT DOCUMENTS

| | | | |
|---|---|---|---|
| 2,708,389 A | 5/1955 | Kavanagh | |
| 3,357,230 A | 12/1967 | Topaz | |
| 3,797,911 A | 3/1974 | Kogelnik et al. | |
| 3,915,573 A | 10/1975 | Knoll et al. | |
| 3,958,252 A | 5/1976 | Kashio | |
| 3,973,118 A | 8/1976 | LaMontagne | |
| 4,081,277 A | 3/1978 | Brault et al. | |
| 4,131,899 A | 12/1978 | Christou | |
| 4,251,733 A * | 2/1981 | Hirleman, Jr. ................ | 250/575 |
| 4,427,296 A | 1/1984 | Demarest et al. | |
| 4,455,089 A | 6/1984 | Yeung et al. | |
| 4,514,257 A | 4/1985 | Karlsson et al. | |
| 4,536,762 A | 8/1985 | Moates | |
| 4,573,796 A | 3/1986 | Martin et al. | |
| 4,715,672 A | 12/1987 | Duguay et al. | |
| 4,730,922 A | 3/1988 | Bach et al. | |
| 4,764,670 A | 8/1988 | Pace et al. | |
| 4,793,705 A | 12/1988 | Shera | |
| 4,820,042 A | 4/1989 | Barger | |
| 4,822,998 A | 4/1989 | Yokota et al. | |
| 4,957,371 A | 9/1990 | Pellicori et al. | |
| 4,959,674 A | 9/1990 | Khuri-Yakub et al. | |
| 4,976,542 A | 12/1990 | Smith | |
| 5,028,545 A | 7/1991 | Soini | |
| 5,080,462 A | 1/1992 | Goto | |
| 5,144,498 A | 9/1992 | Vincent | |
| 5,151,585 A | 9/1992 | Siebert | |
| 5,159,199 A | 10/1992 | Labaw | |
| 5,166,755 A | 11/1992 | Gat | |
| 5,218,426 A | 6/1993 | Hall et al. | |
| 5,243,614 A | 9/1993 | Wakata et al. | |
| 5,254,919 A | 10/1993 | Bridges et al. | |
| 5,281,305 A | 1/1994 | Lee et al. | |
| 5,305,082 A | 4/1994 | Bret | |
| 5,312,535 A | 5/1994 | Waska et al. | |
| 5,324,401 A | 6/1994 | Yeung et al. | |
| 5,370,842 A | 12/1994 | Miyazaki et al. | |
| 5,394,244 A | 2/1995 | Tsai | |
| 5,410,404 A | 4/1995 | Grant | |
| 5,414,508 A | 5/1995 | Takahashi et al. | |
| 5,434,667 A | 7/1995 | Hutchins et al. | |
| 5,437,840 A | 8/1995 | King et al. | |
| 5,445,934 A | 8/1995 | Fodor et al. | |
| 5,491,347 A | 2/1996 | Allen et al. | |
| 5,528,045 A | 6/1996 | Hoffman et al. | |

(Continued)

FOREIGN PATENT DOCUMENTS

| | | |
|---|---|---|
| EP | 0354067 | 2/1990 |
| EP | 0442738 | 8/1991 |

(Continued)

OTHER PUBLICATIONS

European Search Report dated Oct. 18, 2010 issued in EP08150482.1.
Adams et al., "Microfluidic Integration on Detector Arrays for Absorption and Fluorescence Micro-Spectrometers," Sensors and Actuators, 2003, 104:25-31.
U.S. Appl. No. 13/206,436, filed Aug. 9, 2011, Kiesel et al.
U.S. Appl. No. 13/206,439, filed Aug. 9, 2011, Kiesel et al.
U.S. Appl. No. 13/113,021, filed Apr. 19, 2010, Kiesel et al.

(Continued)

*Primary Examiner* — Eric S DeJong
(74) *Attorney, Agent, or Firm* — Hollingsworth Davis, LLC

(57) ABSTRACT

A method is provided for extracting the position of a particle, e.g., a moving or stationary particle that is excited or is emitting light. The method includes, among other steps, detecting and recording a signal based on, for example, the movement of the particle, a correlation step to eliminate noise and to create a transformed signal, a matching or fitting step to match the transformed signal to a fit function and an extracting or determining step to determine the position of the particle from the fit function. In one form, at least two particle positions are detected so that the distance between the subject particles can be determined.

32 Claims, 11 Drawing Sheets

(56) References Cited

U.S. PATENT DOCUMENTS

| | | |
|---|---|---|
| 5,572,328 A | 11/1996 | Fouckhardt et al. |
| 5,608,517 A | 3/1997 | Munk |
| 5,631,734 A | 5/1997 | Stern et al. |
| 5,666,195 A | 9/1997 | Shultz et al. |
| 5,674,698 A | 10/1997 | Zarling et al. |
| 5,677,769 A | 10/1997 | Bendett |
| 5,682,038 A | 10/1997 | Hoffman |
| 5,745,308 A | 4/1998 | Spangenberg |
| 5,760,900 A | 6/1998 | Ito et al. |
| 5,777,329 A | 7/1998 | Westphal et al. |
| 5,784,507 A | 7/1998 | Holm-Kennedy et al. |
| 5,792,663 A | 8/1998 | Fry et al. |
| 5,793,485 A | 8/1998 | Gourley |
| 5,798,222 A | 8/1998 | Goix |
| 5,801,831 A | 9/1998 | Sargoytchev |
| 5,825,792 A | 10/1998 | Villeneuve et al. |
| 5,864,641 A | 1/1999 | Murphy et al. |
| 5,872,655 A | 2/1999 | Seddon et al. |
| 5,876,674 A | 3/1999 | Dosoretz et al. |
| 5,880,474 A | 3/1999 | Norton et al. |
| 5,909,278 A | 6/1999 | Deka et al. |
| 5,917,606 A | 6/1999 | Kaltenbach |
| 5,933,233 A | 8/1999 | Günther |
| 5,945,676 A | 8/1999 | Khalil et al. |
| 5,953,138 A | 9/1999 | Ellis |
| 5,958,122 A | 9/1999 | Fukuda et al. |
| 5,982,478 A | 11/1999 | Ainsworth et al. |
| 5,982,534 A | 11/1999 | Pinkel et al. |
| 6,040,578 A | 3/2000 | Malin et al. |
| 6,049,727 A | 4/2000 | Crothall |
| 6,066,243 A | 5/2000 | Anderson et al. |
| 6,091,502 A | 7/2000 | Weigl et al. |
| 6,108,463 A | 8/2000 | Herron et al. |
| 6,116,718 A | 9/2000 | Peeters et al. |
| 6,122,536 A | 9/2000 | Sun et al. |
| 6,137,117 A | 10/2000 | Feldstein et al. |
| 6,169,604 B1 | 1/2001 | Cao |
| 6,187,592 B1 | 2/2001 | Gourley |
| 6,192,168 B1 | 2/2001 | Feldstein et al. |
| 6,216,022 B1 | 4/2001 | Tyrrell et al. |
| 6,249,346 B1 | 6/2001 | Chen et al. |
| 6,275,628 B1 | 8/2001 | Jones et al. |
| 6,285,504 B1 | 9/2001 | Diemeer |
| 6,295,130 B1 | 9/2001 | Sun et al. |
| 6,306,933 B1 | 10/2001 | Eiger et al. |
| 6,307,623 B1 | 10/2001 | Papuchon et al. |
| 6,310,690 B1 | 10/2001 | Cao et al. |
| 6,353,475 B1 | 3/2002 | Jensen et al. |
| 6,399,405 B1 | 6/2002 | Chen et al. |
| 6,405,073 B1 | 6/2002 | Crowley et al. |
| 6,429,022 B1 | 8/2002 | Kunz et al. |
| 6,438,397 B1 | 8/2002 | Bosquet et al. |
| 6,459,080 B1 | 10/2002 | Yin et al. |
| 6,468,702 B1 | 10/2002 | Yi et al. |
| 6,483,959 B1 | 11/2002 | Singh et al. |
| 6,490,034 B1 | 12/2002 | Woias et al. |
| 6,505,775 B1 | 1/2003 | Gu et al. |
| 6,514,460 B1 | 2/2003 | Fendrock |
| 6,519,037 B2 | 2/2003 | Jung et al. |
| 6,525,308 B1 | 2/2003 | Schmidt-Hattenberger |
| 6,556,854 B1 | 4/2003 | Sato et al. |
| 6,558,945 B1 | 5/2003 | Kao |
| 6,577,780 B2 | 6/2003 | Lockhart |
| 6,580,507 B2 | 6/2003 | Fry et al. |
| 6,603,548 B2 | 8/2003 | Church et al. |
| 6,608,679 B1 | 8/2003 | Chen et al. |
| 6,628,390 B1 | 9/2003 | Johnson |
| 6,630,999 B2 | 10/2003 | Shroder |
| 6,639,679 B2 | 10/2003 | Frojdh |
| 6,665,113 B2 | 12/2003 | Aso et al. |
| 6,678,502 B1 | 1/2004 | Sugaya |
| 6,694,158 B2 | 2/2004 | Polak |
| 6,697,542 B2 | 2/2004 | Platzman et al. |
| 6,704,104 B2 | 3/2004 | Li |
| 6,710,871 B1 | 3/2004 | Goix |
| 6,736,484 B2 | 5/2004 | Nakamura |
| 6,742,884 B2 | 6/2004 | Wong et al. |
| 6,755,983 B2 | 6/2004 | Yudasaka |
| 6,759,713 B2 | 7/2004 | Chabinyc et al. |
| 6,781,690 B2 | 8/2004 | Armstrong et al. |
| 6,785,002 B2 | 8/2004 | Zarrabian et al. |
| 6,795,190 B1 | 9/2004 | Paul et al. |
| 6,796,710 B2 | 9/2004 | Yates et al. |
| 6,800,849 B2 | 10/2004 | Staats |
| 6,806,925 B2 | 10/2004 | Gaudiana et al. |
| 6,809,865 B2 | 10/2004 | Chen |
| 6,815,125 B1 | 11/2004 | Okabe et al. |
| 6,816,257 B2 | 11/2004 | Goix |
| 6,830,856 B2 | 12/2004 | Tsai et al. |
| 6,838,361 B2 | 1/2005 | Takeo |
| 6,839,140 B1 | 1/2005 | O'Keefe et al. |
| 6,856,718 B2 | 2/2005 | Kane et al. |
| 6,865,198 B2 | 3/2005 | Taubman |
| 6,867,420 B2 | 3/2005 | Mathies et al. |
| 6,867,868 B1 | 3/2005 | Barbarossa |
| 6,870,149 B2 | 3/2005 | Berezin |
| 6,872,320 B2 | 3/2005 | Wong et al. |
| 6,872,588 B2 | 3/2005 | Chabinyc et al. |
| 6,887,713 B2 | 5/2005 | Nelson et al. |
| 6,890,050 B2 | 5/2005 | Ready et al. |
| 6,927,852 B2 | 8/2005 | Reel |
| 6,952,603 B2 | 10/2005 | Gerber et al. |
| 6,983,176 B2 | 1/2006 | Gardner et al. |
| 7,011,630 B2 | 3/2006 | Desai et al. |
| 7,024,236 B2 | 4/2006 | Ford et al. |
| 7,034,933 B2 | 4/2006 | Walker et al. |
| 7,064,836 B2 | 6/2006 | Bechtel et al. |
| 7,130,321 B2 | 10/2006 | Spinelli et al. |
| 7,136,161 B2 | 11/2006 | Nakamura |
| 7,149,396 B2 | 12/2006 | Schmidt et al. |
| 7,195,797 B2 | 3/2007 | Mearini et al. |
| 7,252,360 B2 | 8/2007 | Hersch et al. |
| 7,277,569 B2 | 10/2007 | Bruce et al. |
| 7,305,112 B2 | 12/2007 | Curry et al. |
| 7,358,476 B2 | 4/2008 | Kiesel et al. |
| 7,372,435 B2 | 5/2008 | Kim |
| 7,391,517 B2 | 6/2008 | Trebbia et al. |
| 7,420,677 B2 | 9/2008 | Schmidt et al. |
| 7,433,552 B2 | 10/2008 | Kiesel et al. |
| 7,456,953 B2 | 11/2008 | Schmidt et al. |
| 7,466,307 B2 | 12/2008 | Trent, Jr. |
| 7,471,399 B2 | 12/2008 | Kiesel et al. |
| 7,479,625 B2 | 1/2009 | Kiesel et al. |
| 7,496,463 B2 | 2/2009 | Nicoli et al. |
| 7,502,123 B2 | 3/2009 | Kiesel et al. |
| 7,506,268 B2 | 3/2009 | Jennings |
| 7,521,769 B2 | 4/2009 | Cunningham |
| 7,522,786 B2 | 4/2009 | Kiesel et al. |
| 7,545,513 B2 | 6/2009 | Kiesel et al. |
| 7,547,904 B2 | 6/2009 | Schmidt et al. |
| 7,554,673 B2 | 6/2009 | Kiesel et al. |
| 7,633,629 B2 | 12/2009 | Kiesel et al. |
| 7,641,777 B2 | 1/2010 | Joseph et al. |
| 7,694,231 B2 | 4/2010 | Kocienda |
| 7,701,580 B2 | 4/2010 | Bassler et al. |
| 7,718,948 B2 | 5/2010 | Kiesel |
| 7,763,856 B2 | 7/2010 | Kiesel et al. |
| 7,817,254 B2 | 10/2010 | Hegyi et al. |
| 7,817,276 B2 | 10/2010 | Kiesel et al. |
| 7,839,450 B2 | 11/2010 | Hing |
| 7,879,390 B2 | 2/2011 | Saileo et al. |
| 7,894,068 B2 | 2/2011 | Bassler et al. |
| 8,223,127 B2 | 7/2012 | Park |
| 2002/0155485 A1 | 10/2002 | Kao |
| 2003/0000835 A1 | 1/2003 | Witt et al. |
| 2003/0020915 A1 | 1/2003 | Schueller et al. |
| 2003/0077660 A1 | 4/2003 | Pien et al. |
| 2003/0137672 A1 | 7/2003 | Moriya et al. |
| 2003/0161024 A1 | 8/2003 | Zhang et al. |
| 2003/0169311 A1 | 9/2003 | Kong Leong et al. |
| 2003/0178555 A1 | 9/2003 | Fang |
| 2003/0179383 A1 | 9/2003 | Chen et al. |
| 2003/0189711 A1 | 10/2003 | Orr et al. |
| 2003/0191377 A1 | 10/2003 | Robinson et al. |

(56) References Cited

U.S. PATENT DOCUMENTS

| | | |
|---|---|---|
| 2003/0197754 A1 | 10/2003 | Nakamura |
| 2003/0231272 A1 | 12/2003 | Nakamura et al. |
| 2003/0235924 A1 | 12/2003 | Adams et al. |
| 2004/0002225 A1 | 1/2004 | Wong et al. |
| 2004/0027462 A1 | 2/2004 | Hing |
| 2004/0031684 A1 | 2/2004 | Witt |
| 2004/0032584 A1 | 2/2004 | Honda et al. |
| 2004/0038386 A1 | 2/2004 | Zesch et al. |
| 2004/0057050 A1 | 3/2004 | Beck et al. |
| 2004/0067167 A1 | 4/2004 | Zhang et al. |
| 2004/0109659 A1 | 6/2004 | Aylward et al. |
| 2004/0110099 A1 | 6/2004 | Kozawa et al. |
| 2004/0132214 A1 | 7/2004 | Lin et al. |
| 2004/0141884 A1 | 7/2004 | Unno et al. |
| 2004/0145738 A1 | 7/2004 | Sun et al. |
| 2004/0175734 A1 | 9/2004 | Stahler et al. |
| 2004/0178523 A1 | 9/2004 | Kim et al. |
| 2004/0223135 A1 | 11/2004 | Ortyn et al. |
| 2004/0223881 A1 | 11/2004 | Cunningham et al. |
| 2004/0228375 A1 | 11/2004 | Ghosh et al. |
| 2004/0248318 A1 | 12/2004 | Weinberger et al. |
| 2004/0253835 A1 | 12/2004 | Kawase |
| 2005/0042615 A1 | 2/2005 | Smith et al. |
| 2005/0046821 A1 | 3/2005 | Hanson et al. |
| 2005/0068526 A1 | 3/2005 | Arrutshy |
| 2005/0084203 A1 | 4/2005 | Kane |
| 2005/0099624 A1 | 5/2005 | Staehr et al. |
| 2005/0128479 A1 | 6/2005 | Gilbert et al. |
| 2005/0136358 A1 | 6/2005 | Paul et al. |
| 2005/0158868 A1 | 7/2005 | Trebbia et al. |
| 2005/0162648 A1 | 7/2005 | Auer et al. |
| 2005/0162650 A1 | 7/2005 | Yamamoto |
| 2005/0164320 A1 | 7/2005 | McDevitt et al. |
| 2005/0213082 A1 | 9/2005 | DiBernardo et al. |
| 2005/0249605 A1 | 11/2005 | Kane et al. |
| 2005/0255392 A1 | 11/2005 | Tsai et al. |
| 2006/0039009 A1 | 2/2006 | Kiesel et al. |
| 2006/0046312 A1 | 3/2006 | Kiesel et al. |
| 2006/0092413 A1 | 5/2006 | Kiesel et al. |
| 2006/0115749 A1 | 6/2006 | Toyoda |
| 2006/0121555 A1 | 6/2006 | Lean et al. |
| 2006/0138313 A1 | 6/2006 | Tennant et al. |
| 2006/0181710 A1 | 8/2006 | Kachanov et al. |
| 2006/0182659 A1 | 8/2006 | Unlu et al. |
| 2006/0193550 A1 | 8/2006 | Wawro et al. |
| 2006/0203224 A1 | 9/2006 | Sebastian et al. |
| 2006/0268260 A1 | 11/2006 | Liu et al. |
| 2006/0274313 A1 | 12/2006 | Gilbert et al. |
| 2007/0009380 A1 | 1/2007 | Cunningham |
| 2007/0046301 A1 | 3/2007 | Kasapi |
| 2007/0070347 A1 | 3/2007 | Scherer et al. |
| 2007/0076210 A1 | 4/2007 | Kiesel et al. |
| 2007/0096039 A1 | 5/2007 | Kapoor et al. |
| 2007/0116609 A1 | 5/2007 | Baeurle et al. |
| 2007/0145236 A1 | 6/2007 | Kiesel et al. |
| 2007/0145249 A1 | 6/2007 | Kiesel et al. |
| 2007/0146701 A1 | 6/2007 | Kiesel et al. |
| 2007/0146888 A1 | 6/2007 | Schmidt et al. |
| 2007/0147728 A1 | 6/2007 | Schmidt et al. |
| 2007/0165225 A1 | 7/2007 | Trainer |
| 2007/0166725 A1 | 7/2007 | McBride et al. |
| 2007/0172969 A1 | 7/2007 | Wong et al. |
| 2007/0186791 A1 | 8/2007 | Kim et al. |
| 2007/0201025 A1 | 8/2007 | Greenwald |
| 2008/0013092 A1 | 1/2008 | Matezos et al. |
| 2008/0095985 A1 | 4/2008 | Frey et al. |
| 2008/0179541 A1 | 7/2008 | LeBoeuf et al. |
| 2008/0181827 A1 | 7/2008 | Bassler et al. |
| 2008/0183418 A1 | 7/2008 | Bassler et al. |
| 2008/0186483 A1 | 8/2008 | Kiesel et al. |
| 2008/0186494 A1 | 8/2008 | Kiesel et al. |
| 2008/0186504 A1 | 8/2008 | Kiesel et al. |
| 2008/0186511 A1 | 8/2008 | Kiesel et al. |
| 2008/0187011 A1 | 8/2008 | Kiesel et al. |
| 2008/0213915 A1 | 9/2008 | Durack et al. |
| 2009/0016672 A1 | 1/2009 | Schmidt et al. |
| 2009/0016690 A1 | 1/2009 | Schmidt et al. |
| 2009/0108214 A1 | 4/2009 | Shinoda et al. |
| 2009/0220189 A1 | 9/2009 | Kiesel et al. |
| 2010/0108910 A1 | 5/2010 | Morrell et al. |
| 2010/0155572 A1 | 6/2010 | Kiesel et al. |
| 2010/0155577 A1 | 6/2010 | Kiesel et al. |
| 2010/0157291 A1 | 6/2010 | Kiesel et al. |
| 2010/0201988 A1 | 8/2010 | Kiesel |
| 2010/0256943 A1 | 10/2010 | Donnenberg et al. |
| 2010/0261288 A1 | 10/2010 | Recknor et al. |
| 2011/0118571 A1 | 5/2011 | Mandelis et al. |
| 2011/0222062 A1 | 9/2011 | Martini et al. |
| 2013/0037726 A1 | 2/2013 | Kiesel et al. |
| 2013/0037728 A1 | 2/2013 | Kiesel et al. |
| 2013/0200277 A1 | 8/2013 | Li et al. |

FOREIGN PATENT DOCUMENTS

| | | |
|---|---|---|
| EP | 0678881 | 11/1995 |
| EP | 1324018 | 7/2003 |
| EP | 1653217 | 6/2007 |
| EP | 1800752 | 6/2007 |
| EP | 1801553 | 6/2007 |
| EP | 1801562 | 6/2007 |
| EP | 1801564 | 6/2007 |
| EP | 1950552 | 7/2008 |
| JP | 02049143 | 2/1990 |
| JP | 02245638 | 10/1990 |
| JP | 2245638 | 10/1990 |
| JP | 03020642 | 1/1991 |
| JP | 3020642 | 1/1991 |
| JP | 04223261 | 8/1992 |
| JP | 04297888 | 10/1992 |
| JP | 05240774 | 9/1993 |
| JP | 06018421 | 1/1994 |
| JP | 08233788 | 9/1996 |
| JP | 08261922 | 10/1996 |
| JP | 2001044114 | 2/2001 |
| JP | 2004252214 | 9/2004 |
| JP | 2005165073 | 6/2005 |
| JP | 2007518991 | 6/2007 |
| WO | WO9520144 | 7/1995 |
| WO | WO9944042 | 9/1999 |
| WO | WO9954730 | 10/1999 |
| WO | WO0039573 | 7/2000 |
| WO | WO0062050 | 10/2000 |
| WO | WO0217219 | 2/2002 |
| WO | WO0225269 | 3/2002 |
| WO | 2004033059 | 4/2004 |
| WO | WO2004063681 | 7/2004 |
| WO | WO2004083820 | 9/2004 |
| WO | WO2005017498 | 2/2005 |
| WO | WO2005068971 | 7/2005 |
| WO | WO2005108963 | 11/2005 |
| WO | WO2006083969 | 8/2006 |
| WO | WO2006133360 | 12/2006 |
| WO | WO2007069840 | 6/2007 |

OTHER PUBLICATIONS

Bese et al., "A compact, affordable and portable CD4 T-cell machine", Int. Conf. AIDS 2002, Jul. 7-12, 2002, 1 pg.

Henry et al., "Wavelength Response of Thin-Film Optical Postition-Sensitive Detectors", J. Opt. A: Pure Appl. Opt., Vole. 4, 2002, pp. 527-534. (abstract only).

Imade et al., "Comparison of a New, Affordable Flow Cytometric Method and the Manual Magnetic Bead Technique for CD4 T-Lymphocyte Counting in a Northern Nigerian Setting", Clinical and Diagnostic Laboratory Imm., Jan. 2005, p. 224-227.

Kiesel et al., "Hand-held flow cytometer for point of care CD4 testing", APS March Meeting 2010, vol. 55, No. 2. (abstract only).

Kiesel et al., "Spatially modulated fluorescence emission from moving particles", Applied Physics Letters, vol. 94, 2009, 3 pages.

Kiesel et al., "Spatially Modulated Emission Advances Point-of-Care Diagnostics", Laser Focus World, Nov. 2010, pp. 47-50.

"Optical Chopper—SR540—Optical Chopper System", Stanford Research Systems, 2008, 2 pages.

(56) References Cited

OTHER PUBLICATIONS

File History for U.S. Appl. No. 12/024,490.
File History for U.S. Appl. No. 12/025,394.
File History for U.S. Appl. No. 12/023,436.
File History for U.S. Appl. No. 12/022,485.
File History for U.S. Appl. No. 12/762,702.
File History for EP Application No. 09151643.5 as retrieved from the European Patent Office electronic file system on Mar. 22, 2013, 133 pages.
File History for EP Application No. 08150482.1 as retrieved from the European Patent Office electronic file system on Mar. 22, 2013, 82 pages.
File History for U.S. Appl. No. 13/206,439.
Adams et al., "Microfluidic Integration on Detector Arrays for Absorption and Fluorescence Micro-spectrometer", Sensors and Actuators, 2003, pp. 25-31.
Agilent Technologies, "Agilent 83453B High-Resolution Spectrometer—Technical Specifications", Feb. 2005, pp. 1-8.
Agilent Technologies "Developing Technology: HPLC-Chip/MS", May 25, 2011, 2 pages.
Bassler et al., "Class Identification of Bio-Molecules Based on Multicolor Native Fluorescence Spectroscopy", International Journal of High Speed Electronics and Systems, vol. 17, Issue 4, 2007, pp. 671-680.
Becker et al., "Polymer Microfabrication Methods for Microfluidic Analytical Applications", Electrophoresis, vol. 21, 2000, pp. 12-26. (abstract only).
Bernini et al., "Silicon Micromachined Hollow Optical Waveguides for Sensing applications", IEEE Journal on Selected Topics in Quantum Electronics, vol. 8, No. 1, Jan./Feb. 2002, pp. 106-110. (abstract only).
Bhatta et al., "Rapid Identification of Microorganisms by Intrinsic Fluorescence", Proc. of SPIE, vol. 5699, 2005, pp. 9-18.
Bracewell, R.N., The Fourier Transform and Its Applications, $2^{nd}$ Ed., McGraw-Hill, 1978, Table of Contents and pp. 24-50, 98-126, and 177-188. (No copy available).
Cheung et al., "Impedance Spectroscopy Flow Cytometry: On-Chip Label-Free Cell Differentiation", Cytometry Part A, vol. 65A, 2005, pp. 124-132.
Cunningham et al., "Label-Free Assays on the Bind System", Journal of Biomolecular Screening, vol. 9, No. 6, 2004, pp. 481-490.
Devasenathipathy et al., "3 Electrokinetic Flow Diagnostics", in Breuer K.S. Ed. Micro-and Nano-Scale Diagnostic Techniques, Springer Verlag, New York, 2003, pp. 121-166.
Fuhr, Measuring with Light, Sensors Magazine Online, May 2000, 11 pages.
Fuji-Keizai USA, "Biosensor Market, R&D and Commercial Implication", 2004, 5 pages.
Hoffman, R. A., "Flow Cytometry: Instrumentation, Applications, Future Trends and Limitations", Springer Series on Fluorescence, vol. 6, 2008, pp. 307-342.
Holmes et al., "Label-Free Differential Leukocyte Counts Using a Microfabricated, Single-Cell Impedance Spectrometer", Sensors, 2007 IEEE, pp. 1452-1455. (abstract only).
Janossy et al., "Affordable CD4+-T-Cell Counting by Flow Cytometry:CD45 gating for Volumetric Analysis", Clinical and Diagnostic Laboratory Immunology, Sep. 2002, p. 1085-1094.
Johnson et al., "Introductions to Photonic Crystals: Bloch's Theorem, Band Diagrams, and Gaps (But No Defects)", Feb. 3, 2003, 16 pages.
Johnson, "Photonic Crystals: Periodic Surprises in Electromagnetism", printed from ab-initio.mit.edu on Oct. 5, 2006, 3 pages.
Jones et al., "Dielectrophoretic Liquid Actuation Nanodroplet Formation", Journal of Applied Physics, vol. 89, No. 2, 2001, pp. 1441-1448. (abstract only).
Kalvaram et al., "Precision moulding techniques for optical waveguide devices", SPIE, vol. 3135, 1997, pp. 2-11. (no copy available).
Konsziela, "Accurately Measure Laser Spectral Characteristics", 2006, 5 pages.

2005, Kim et al., "Polymer-Planar-Lightwave-Circuit-Type Variable Optical Attenuator Fabricated by Hot Embossing Process" ETRI Journal, vol. 27, No. 1, Feb. 2004, pp. 10-16.
Law et al., "Low-Voltage Superlattice Asymmetric Fabry-Perot Reflection Modulator", IEEE Phot. Tech. Lett, vol. 3, No. 4, Apr. 1991, pp. 324-326. (abstract only).
Liang et al., "Refractive Index Measurement of Single Living Cell Using a Biophotonic Chip for Cancer Diagnosis Applications", $9^{th}$ International Conference on Miniaturized Systems for Chemistry and Life Sciences, Oct. 2005, 3 pages.
Liu et al., "Nanowell Surface Enhanced Raman Scattering Arrays Fabricated by Soft-Lithography for Label-Free Biomolecular Detections in Integrated Microfluidics", Applied Physics Letters, vol. 87, 2005, pp. 1-3.
McNichols et al., "Optical Glucose Sensing in Biological Fluids: An Overview", Journal of Biomedical Optics, vol. 5, No. 1, Jan. 2000, pp. 5-16. (abstract only).
Othonos et al. "Fiber-Bragg Gratings—Fundamentals and Applications in Telecommunications and Sensing", Artech House, Norwood, MA, 1999, pp. 304-330. (no copy available).
Prassad, "Introduction to Biophotonics", John Wiley & Sons, Hoboken, N.J. 2003, pp. 311-356. (no copy available).
Schaefer et al., "Accuracy of Position Detection Using a Position-Sensitive Detector", IEEE Transactions on Instrumentation and Measurement, vol. 47, No. 4, Aug. 1998, pp. 914-919. (abstract only).
Schmidt et al., "Guiding Light in Fluids", applied Physics Letters, vol. 88, 2006, pp. 151109-1-1151109-3.
Schmidt et al., "Enhanced light-target interaction using a novel anti-resonant waveguide concept", SPIE Proc. 6094, 2006, pp. 80-89.
Schmidt et al., "Fluorescence Spectrometer-on-a-fluidic-chip", Lab Chop, 2007.
1999, Seamer et al., "Sheath Fluid control to Permit Stable Flow in Rapid Mix Flow Cytometry", Cytometry, vol. 5699, 2005, pp. 75-79.
Shapiro, "Practical flow Cytometry", $4^{th}$ Edition, Wiley-Liss, 2003, Table of contents and pp. 49-59, 124-183, 191-197, and 364-366. (no copy available).
Shaw et al., "Optomechanical design of tunable Ip-based Fabry-Perot filters for WDM applications", Journal of Microlithography, vol. 4, Oct.-Dec. 2005, pp. 041303-1-041303-8. (no copy available).
Sims et al., "Analysis of Single Mammalian Cells On-Chip", Lab Chip., vol. 7, Issue 4, Apr. 2007, pp. 423-440. (Abstract only).
Singh et al., "Analysis of cellular Structure by Light Scattering Measurements in a New Cytometer Design Based on a Liquid-Core Waveguide", IEEE Proceedings Nanobiotechnology, vol. 151, No. 1, Feb. 2004, pp. 10-16.
Singh et al., "Leaky ARROW Waveguides for Optical Chemical and Biosensors", 1998.
Sivaprakasam et al., "Multiple UV Wavelength Excitation and Fluorescence of Bioaerosols", $2^{nd}$ Joint conference on Point Detections, Williamsburg, VA 2004, 10 pages. (no copy available).
Spear et al., "Low noise position sensitive detector for optical probe beam deflection measurements", Rev. Sci. Instrum., vol. 67, No. 7, Jul. 1996, pp. 2481-2484. (abstract only).
SRU Biosystems, Inc., "BIND Biosensor TM Technology", Apr. 3, 2004 excerpt, 1 page.
Udd, "Good Sense", SPIE's OEMagazine, Aug. 2002, pp. 27-29.
Vogel, "Tunable Liquid Crystal Fabry-Perot Filters", Institute for Electrical and Optical Communication Engineering, University of Stuttgart, 2002, 10 pages. (abstract only).
Vollmer et al., "Multiplexed DNA Quantification by Spectroscopic Shift of Two Microsphere Cavities", Biophysical Journal, vol. 85, Sep. 2005, pp. 106.
Weismann et al., "Singlemode polymer waveguides for optical backplanes", Electronics Letters, vol. 32, No. 25, Dec. 5, 1996, pp. 2329-2330. (abstract only).
Wippich et al., "Tunable and Fiber-Bragg-Grating Sensors", The Industrial Physicist, Jun./Jul. 2003, pp. 24-27. (no copy available).
File History for U.S. Appl. No. 14/474,742.
File History for U.S. Appl. No. 14/155,094.
File History for U.S. Appl. No. 13/113,021.
File History for U.S. Appl. No. 11/698,409.
File History for U.S. Appl. No. 13/206,436.
File History for U.S. Appl. No. 12/337,737.

(56) References Cited

OTHER PUBLICATIONS

File History for U.S. Appl. No. 12/337,796.
File History for U.S. Appl. No. 12/337,771.
File History for EP Application No. 09151643.5 as retrieved from the European Patent Office electronic file system on Jun. 27, 2013, 138 pages.
File History for EP Application No. 08150482.1 as retrieved from the European Patent Office electronic file system on Jun. 27, 2013, 82 pages.
2005, "Abstracts of Published Work", dias.umist.ac.uk, 3 pages. (No copy available).
2005, Goddard et al., Anti-Resonant Reflecting Optical Waveguides (ARROW), as Optimal Optical Detectors for MicroTAS Applications, dias.umist.ac.uk, 5 pages.
Koch et al., "Design and fabrication of a micromachined Coulter counter", J. Micromech. Microeng. 9, 1999, pp. 159-161. (No copy available).
"Lab-on-a-Chip, Advances in Microarray Technology and Advances in Biodefense Technology", brochure, May 7-8, 2008, 6 pages. (No copy available).
Murata, "Spectral Images Camera Using Linear Variable Interference Filter", Oct. 2003, 6 pages.
2006, Sailor, M.J., "Nanostructured Sensors—"Smart Dust"", www.chem.ucsd.edu, 2 pages. (No copy available).
Xu et al., "Research of Image Spectrometer Using Linear Variable Interference Filter", Spectroscopy and Spectral Analysis, vol. 22, No. 5, p. 713-717. Oct. 2002.
File History for EP Application No. 09151643.5 as retrieved from the European Patent Office electronic file system on Feb. 21, 2014, 149 pages.

\* cited by examiner

METHOD AND SYSTEM FOR EVALUATION OF SIGNALS RECEIVED FROM SPATIALLY MODULATED EXCITATION AND EMISSION TO ACCURATELY DETERMINE PARTICLE POSITIONS AND DISTANCES

CROSS REFERENCE TO RELATED PATENTS AND APPLICATIONS

This application is related to U.S. application Ser. No. 11/698,409, entitled "Method and System Implementing Spatially Modulated Excitation or Emission for Particle Characterization with Enhanced Sensitivity," filed on even date herewith.

BACKGROUND

There is a desire to detect the precise location and/or distance between particles on a micro-scale. One example of this resides in the use of fluorescent tags on linearized DNA strings based on a spatially modulated excitation. A system and method for detecting such particles or tags is described in U.S. Publication No. 2008/0181827 filed on even date herewith and incorporated herein by reference.

In an example of the cited application above, with reference to FIG. 1, a system 10 having a DNA string 12 with fluorescent tags 14 typically moves down a channel 16. The channel 16 guides the string 12 through an excitation stripe pattern 18 of a detection area 20. A detector 22 is suitably positioned relative to the detection area 20. The fluorescent signal resulting from the spatial modulation of the stripe pattern (or other suitable pattern, or technique, or architecture) is recorded vs. time as depicted in FIG. 2. A processing module 21 is also shown and is operative to conduct processing on the signal. The signal has a complex shape and, in one form, may be processed, for example, to resolve the positions of the tags 14. The positions of the tags are meaningful data in the contemplated DNA analysis. However, determining these positions becomes particularly difficult if two tags 14 are within the detection area at the same time (as in FIG. 3) and/or if the signal is noisy (as in FIG. 4).

The desire to determine particle position arises in other experimental environments. For example, the positions of particles are used in particle counting and cell sorting processes. Further, the actual or relative positions of particles on, for example, a microscope slide may be useful for certain diagnostic analyses. Examples of systems that may be used in such environments are also disclosed in U.S. Publication No. 2008/0181827 filed on even date herewith and incorporated herein by reference.

INCORPORATION BY REFERENCE

U.S. Publication No. 2008/0181827 is incorporated herein by reference.

BRIEF DESCRIPTION

In accordance with one aspect of the presently described embodiments, the method comprises detecting a particle based on a spatial modulation, recording a time modulated signal based on the detecting of the particle, applying a correlation routine to the time modulated signal to generate a transformed signal, applying a fit function to the transformed signal, and, extracting the position of the particle based on the applying of the fit function.

In accordance with another aspect of the presently described embodiments, the applying of the correlation routine comprises applying a test function to the recorded signal and integrating the recorded signal over time.

In accordance with another aspect of the presently described embodiments, two positions are detected in order to calculate the distance between both positions.

In accordance with another aspect of the presently described embodiments, the particle is a DNA sequencing tag and the detecting is based on an optical bar code read out.

In accordance with another aspect of the presently described embodiments, the particle is disposed on a biochip.

In accordance with another aspect of the presently described embodiments, the fit function is a triangle.

In accordance with another aspect of the presently described embodiments, a method comprises detecting a particle based on a spatial modulation, recording a time modulated signal based on the detecting of the particle, calculating a sliding integral overtime on the recorded signal, applying a fit function to the sliding integral to obtain an estimated position of the particle, calculating a correlation signal, calculating a derivative signal of the correlation signal, determining a maximum and a minimum of the derivative signal based on the estimated position of the particle, and, determining a zero transition to determine a calculated position of the particle.

In accordance with another aspect of the presently described embodiments, the fit function is a triangle.

In accordance with another aspect of the presently described embodiments, the method further comprises determining the slope of flanks of the triangle to determine if multiple particles are present.

In accordance with another aspect of the presently described embodiments, the method further comprises integrating the triangle to determine if multiple particles are present.

In accordance with another aspect of the presently described embodiments, the determining comprises determining multiple maximums and minimums to determine the positions of multiple particles.

In accordance with another aspect of the presently described embodiments, the method is applied in two dimensions to determine a location of the particle.

In accordance with another aspect of the presently described embodiments, the method further comprises the use of least squares fitting of a measured signal to determine the positions of multiple particles that are within a predetermined distance from one another.

In accordance with another aspect of the presently described embodiments, the time modulated signal is based on a detected optical signal.

In accordance with another aspect of the presently described embodiments, the optical signal is a light signal.

In accordance with another aspect of the presently described embodiments, the time modulated signal is based on a detected non-optical signal.

In accordance with another aspect of the presently described embodiments, the correlation signal is based on a chirp signal.

In accordance with another aspect of the presently described embodiments, the time modulated signal is periodic.

In accordance with another aspect of the presently described embodiments, the time modulated signal is based on a known signal.

In accordance with another aspect of the presently described embodiments, a system comprises means for detecting a particle, means for recording a signal based on the detecting, means for applying a correlation routine to the signal to generate a transformed signal, means for applying a fit function to the transformed signal, and, means for extracting the position of the particle based on the applying of the fit function.

In accordance with another aspect of the presently described embodiments, the means for applying of the correlation routine comprises means for applying a test function to the recorded signal and means for integrating the recorded signal over time.

In accordance with another aspect of the presently described embodiments, the particle is a DNA sequencing tag.

In accordance with another aspect of the presently described embodiments, the particle is disposed on a biochip.

In accordance with another aspect of the presently described embodiments, the fit function is a triangle.

In accordance with another aspect of the presently described embodiments, a system comprises means for detecting a particle, means for recording a signal based on the detecting, means for calculating a sliding integral over time on the recorded signal, means for applying a fit function to the sliding integral to obtain an estimated position of the particle, means for calculating a correlation signal, means for calculating a derivative signal of the correlation signal, means for determining a maximum and a minimum of the derivative signal based on the estimated position of the particle, and, means for determining a zero transition to determine a calculated position of the particle.

DETAILED DESCRIPTION

According to the presently described embodiments, a method is provided for extracting the position of a particle, e.g., a moving or stationary particle that is excited or is emitting light. The method, in one form, includes, among other techniques, detecting and recording a signal based on, for example, the movement of the particle, a correlating step to eliminate noise and to create a transformed signal, matching or fitting to match the transformed signal to a fit function and extract or determine the position of the particle from the fit function. In one form, at least two particle positions are detected so that the distance between the subject particles and their individual positions can be determined independently.

Figure 1:
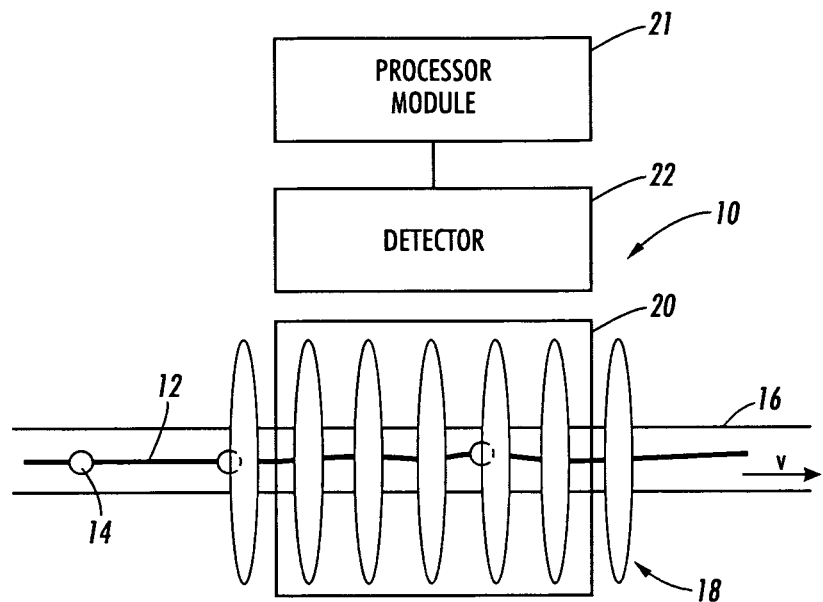
FIG. 1 illustrates a detection area of a system for detecting particles.

In addition, it should be appreciated that particles may be detected and signals may be generated using a variety of systems, including those systems described in U.S. Publication No. 2008/0181827 filed on even date herewith which is incorporated herein by reference. Also, the techniques for characterizing particles as described herein may be implemented using a variety of hardware configurations and/or software techniques. For example, software routines may be implemented using a processing module, such as processing module 21 of FIG. 1 and other processing modules shown in the above-noted patent application.

It should be appreciated that some forms of the presently described embodiments may be applicable to periodic signals; however, an otherwise coded signal may also be processed in order to determine locations and/or relative positions of particle(s). In this regard, the coding of the signal should be known.

The generated signal can have any shape as a function of time. It need not necessarily be strictly periodic. Even a signal modulated randomly is useful as long as the structure of the signal is known. In this regard, the structure may be known but the signal may not follow an analytic regularity. So, the time periods defining "on" and "off" states for the particle will have a random length. Even where the time dependence of the signal is built into the system, the time dependence of the system can be varied so long as it is known (or predictable).

Note that different encodings of the signal (e.g., chirped or strictly periodic) carry specific advantages for a particular application. Chirped signals improve spatial resolution and particle separation. Strictly periodic signals allow determination of particle speed and are more adaptive to particles with different speeds.

Figure 15:
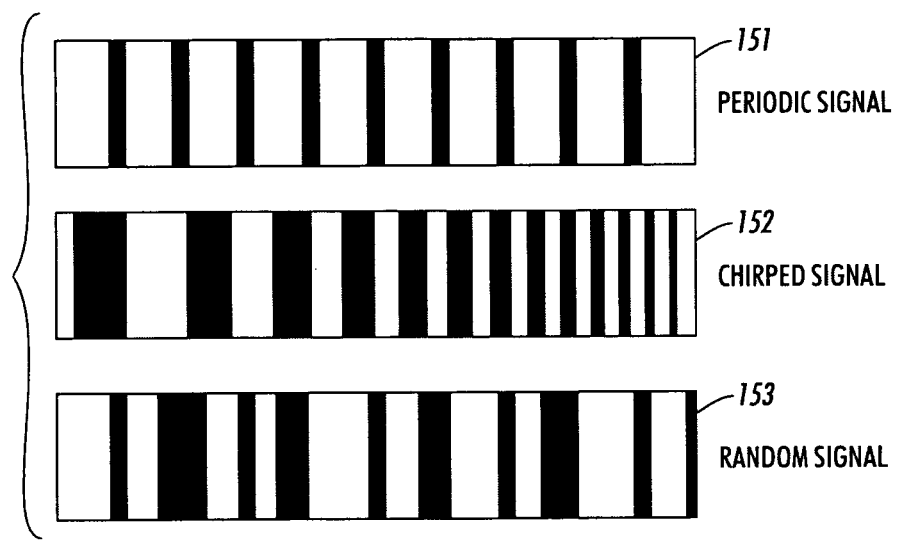

To explain, with reference to FIG. 15, various types of signals that may be generated and used in the presently described embodiments are illustrated. For example, signal 15-1 is a periodic signal. Signal 15-2 is a chirped signal, e.g., a signal that has a linearly increasing frequency. Also shown is a random signal 15-3. It should be appreciated that these signals (as well as others) may be used in connection with the presently described embodiments to achieve the objectives of the presently described embodiments.

It should also be appreciated that the presently described embodiments may be used to determine the actual position of single particles, as well as the relative positions and distance between multiple particles, based on a time modulated signal produced (in at least one form) from a spatial modulation of the emission or excitation of the particle. Still further, the techniques described herein can be applied in two dimensions. In at least one form, analysis can be accomplished in one direction and then applied a second time in a perpendicular second direction.

The presently described embodiments are, in at least one form, applied to analytical techniques that involve particles included within flowing fluid. However, it should be appreciated that the presently described embodiments may also be applied where the particles are relatively stationary in, for example as noted above, within a fluid in a microscope slide. In such a case, the slide or the detector may be set in motion, as opposed to the fluid being in motion by way of its flow. Of course, this type of analysis may also be applied in two dimensions. In this regard, the particle(s) of interest may be localized by conducting the analysis in one direction, and then conducting the analysis in a second direction perpendicular to the first direction.

Implementation of the presently described embodiments has wide application. For example, the presently described embodiments may be applied to DNA identifying methods, as well as other data analyses of signals generated in connection with bio-chips. Still further, the techniques of the presently described embodiments may be applied to analyses wherein particles are located among other particles, such as in cell sorting or particle counting techniques. In these cases, the actual position or distance between particles may be determined.

Figure 2:
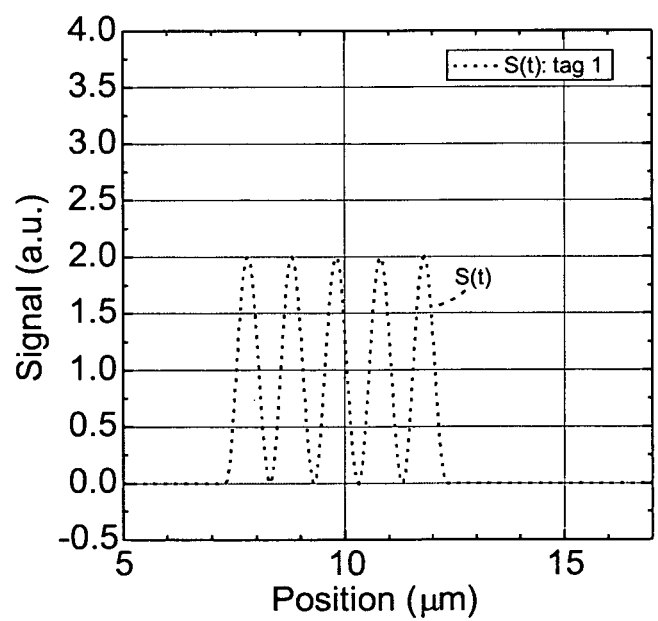
FIG. 2 is a graph illustrating a signal from a particle detected with the system of FIG. 1.
Figure 3:
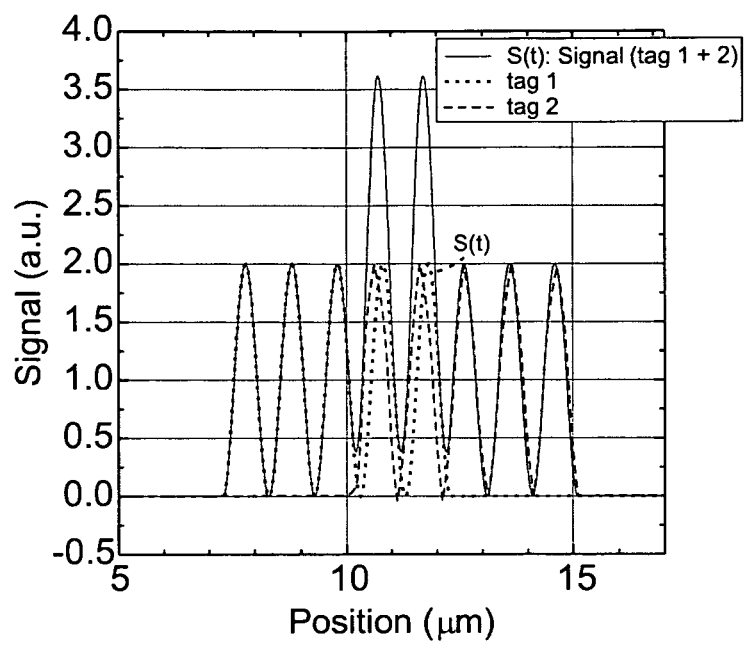
FIG. 3 is a signal from two particles detected with the system of FIG. 1.
Figure 4:
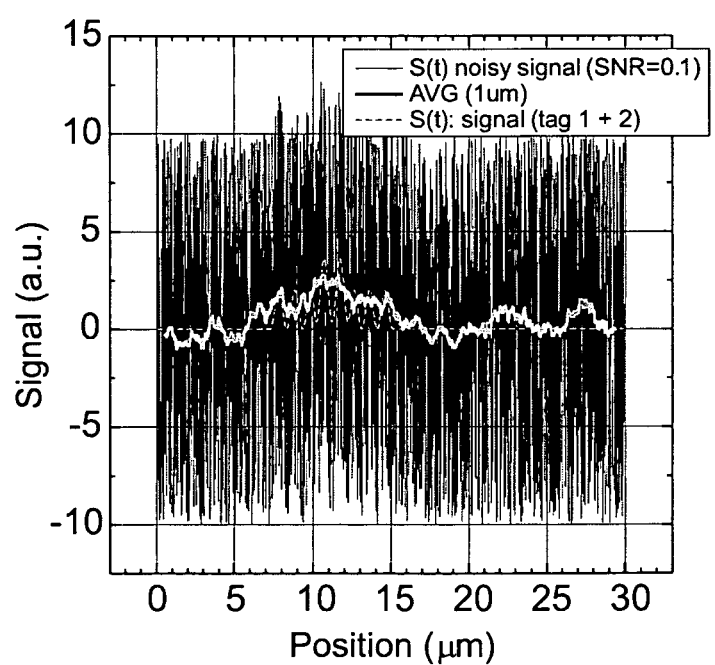
FIG. 4 is a signal from two particles detected with the system of FIG. 1 where noise is present.

With reference now back to the drawings, an exemplary method for detecting the position of DNA tags is described. Of course, it should be understood that this process may also be applied to other environments. In this example, a signal (such as that shown in FIG. 3 or 4) is first processed using a system such as that shown in FIG. 1, according to the presently described embodiments, with a correlation technique, taking advantage of the fact that the signal contains a certain known shape and periodicity. In this example, each fluorescence tag produced 5 equidistant intensity peaks (such as in FIG. 2).

An exemplary procedure for the signal processing is as follows: The time-dependent signal S(t) corresponding, for example, to the spatial modulation of the excited tags (shown in various forms in FIGS. 2-4), is multiplied with a test function P(t), which is restricted to a small window in time of the signal, and subsequently integrated. The test window is then shifted by one time interval and processed in the same way again. This is done for all time intervals. The following equation describes how the resulting correlation signal L(t) is calculated.

$$L(t) = \int_{t-\tau}^{t} S(\tau) P(\tau - t + T) d\tau$$

Figure 5:
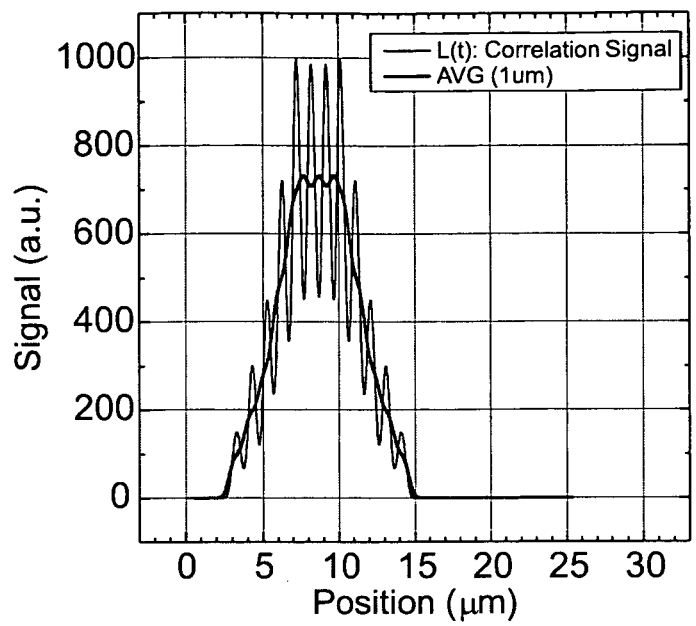
FIG. 5 is a signal used in the presently described embodiments.
Figure 6:
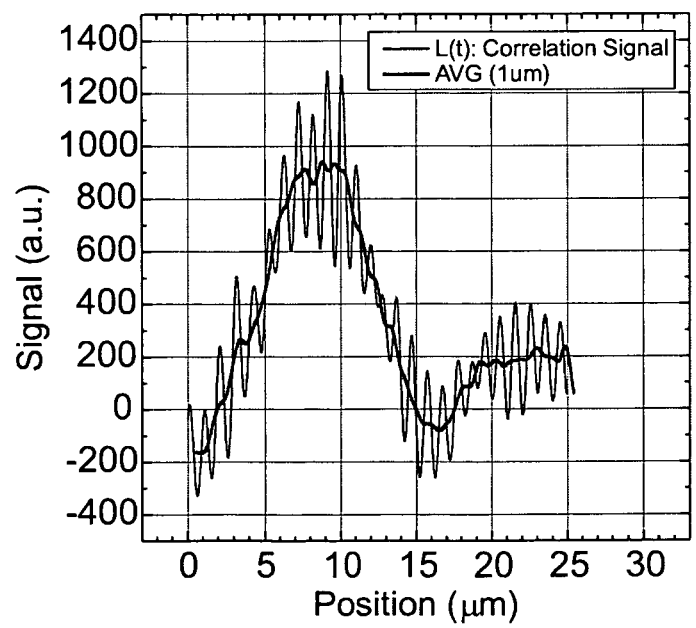
FIG. 6 is a signal used in connection with the presently described embodiments.

For the following example, a sinusoid was used as test function with a periodicity identical to the signal frequency. The integration window T was chosen to cover 5 periods of the sinusoid. FIG. 5 shows the resulting signal L(t) without noise whereas FIG. 6 shows the same evaluation with noise added to the original signal.

In order to determine the precise position of the tags on the DNA, the correlation signal is further processed. The analysis can be done, using a variety of signal processing algorithms, including Fourier-Transformation analysis or Least-Square fitting techniques. The latter one has been used in the following example.

A triangular function f(t) is fitted to the correlation signal. In this specific example, two particles are within the detection area at the same time. The correlation signal is thus fitted with the sum of two triangles. The position $(t_1, t_2)$ of the two triangles is varied independently in order to minimize the deviations between the correlation signal and the sum of the triangle functions. In other words, $t_i$ is varied in order to minimize $\chi^2$, where i is the number of a particle with $$\chi^2 = \sum_t \left( L(t) - \sum_i (t - t_i) \right)^2$$

Figure 7:
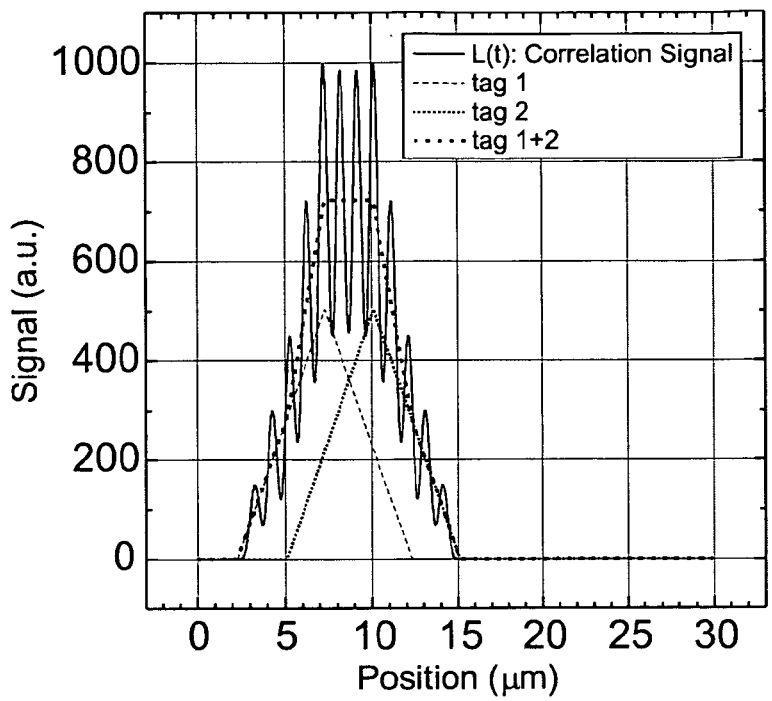
FIG. 7 is a signal shown in FIG. 5 having applied thereto the presently described embodiments.
Figure 8:
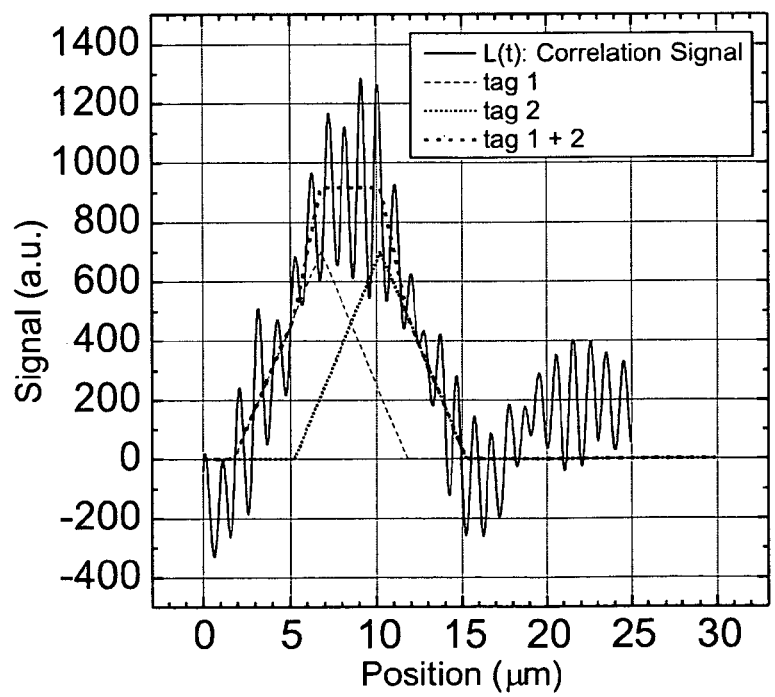
FIG. 8 is the signal of FIG. 6 having applied thereto the presently described embodiments; and, FIG. 9 is a signal used in connection with the presently described embodiments.

FIGS. 7 and 8 shows the two triangles as well as the sum of both triangles for the case without and with noise, respectively. The position of the tip of the triangles identifies the original position of the fluorescent tags.

The following table indicates the real positions of the fluorescent tags as well as the deconvoluted positions for both discussed cases. Without noise, the positions received from the deconvoluted signal match perfectly with the real positions of the fluorescent tags. In the noisy case, the deviation is larger but still smaller than 1, meaning that in this case the position error is still smaller that the periodic constant from the excitation pattern. This is sufficient for most applications.

| | Real position | Position of deconvoluted signal without noise | Position of deconvoluted signal with noise (SNR = 0.1) |
| --- | --- | --- | --- |
| Tag 1 | 7.30 | 7.29 | 6.80 |
| Tag 2 | 10.10 | 10.11 | 10.25 |

It should be understood that very specific choice of functions for P(t) and f(t) has been made to demonstrate this technique. Many other functions can be chosen to similarly solve the discussed problem.

According to the presently described embodiments, correlation techniques can be applied to eliminate noise from the recorded time-dependent fluorescence. Even with a SNR=0.1, signal processing is still very reliable.

Moreover, the location of a fluorescence particle can be extracted precisely from the time-dependence of the fluorescence signal (even in the case of extremely high noise). Also, the positions of several fluorescent particles which are within the interference pattern simultaneously can be determined.

As noted, the above techniques can be modified to be implemented in a variety of different circumstances. One such modification may involve generalizing the above technique to evaluate the position of a single particle that may not produce a periodic signal, but another signal with known time dependence.

Figure 9:
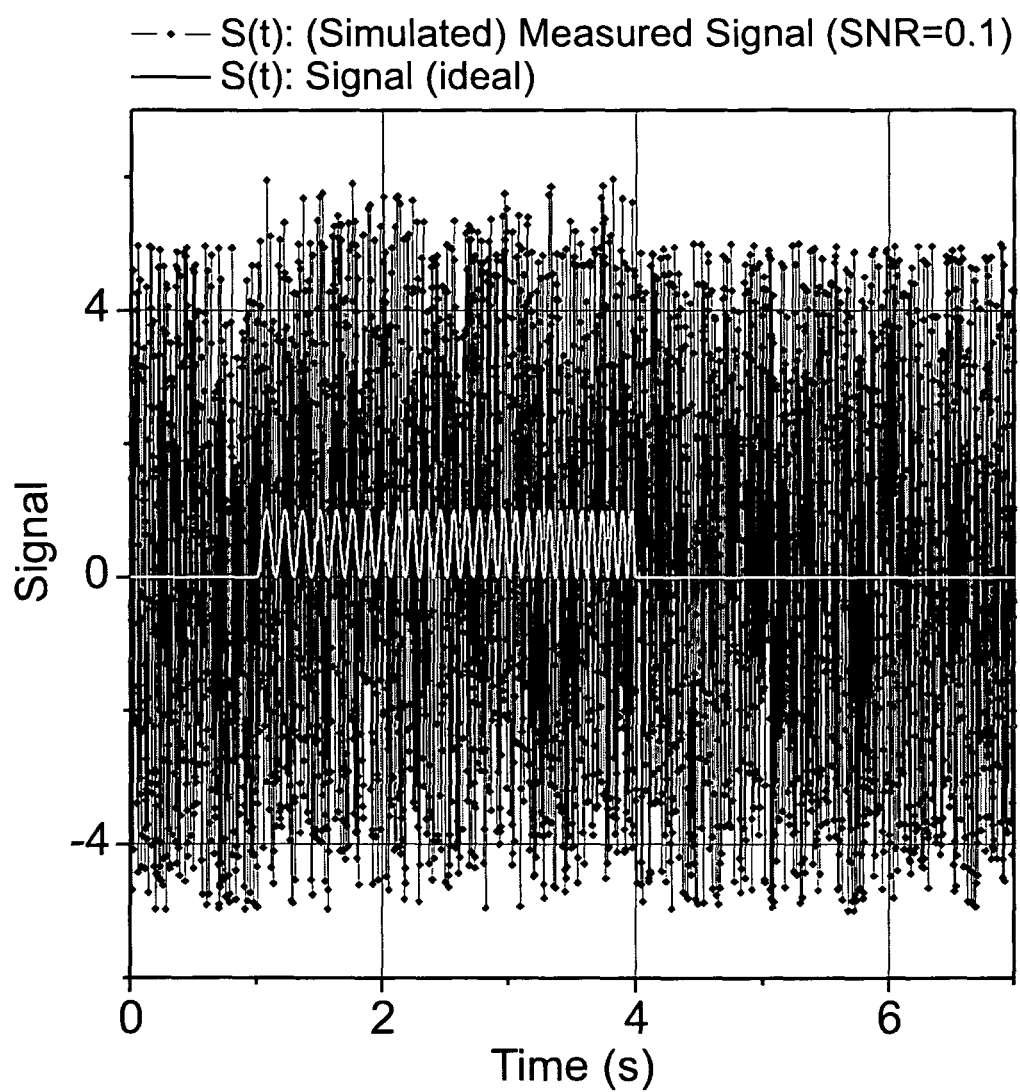

In this regard, with reference to FIG. 9, a chirped signal is used. In this exemplary context, the chirped signal is a non-periodic signal where the duration of each detection of light (e.g. 29 peaks) from the particle decreases by a factor of two over the entire signal length T (e.g. 3 seconds). In other words, the frequency of the signal increases from a minimum frequency $f_{min}$ linearly to a maximum frequency $f_{max}$. An ideal signal of this type is plotted in FIG. 9.

In this example, the particle is detected by an appropriate sensor and the resultant signal is recorded, as shown in FIG. 9. As noted, many different systems can be used to accomplish this recording, including those systems described in U.S. Publication No. 2008/0181827 filed on even date herewith which is incorporated herein by reference.

It should be appreciated that the resultant signal may be generated by virtue of a variety of different patterns and/or associated architectures and/or techniques. However, in at least one form, the overall pattern has a size larger than the particle size. Further, the minimum spacing of the features of the pattern (e.g. the stripes of a pattern as in FIG. 1) is greater than or equal to the particle size. Patterns of such configuration are advantageous to gain a relatively high spatial resolution, so that information may be had from the resulting signal that will be useful for determining precise locations and positions. In at least one form of the presently described embodiments, determining that a particle is simply within a pattern is insufficient—determining precise locations and positions is an objective. For consistency, to determine a particle position with respect to other particles, or the environment, measurements of time are taken as the particle exits the pattern. Of course, other conventions may be used.

The generalized technique described hereafter has, in at least one form, two basic components: 1) determining the existence and estimated position of a particle (as in FIGS. 1-8), and 2) determining particle position to a higher accuracy by applying a correlation technique to the measured signal. It should be understood that exercising the first component of the technique reduces computational effort and, thus, saves system resources.

Figure 10:
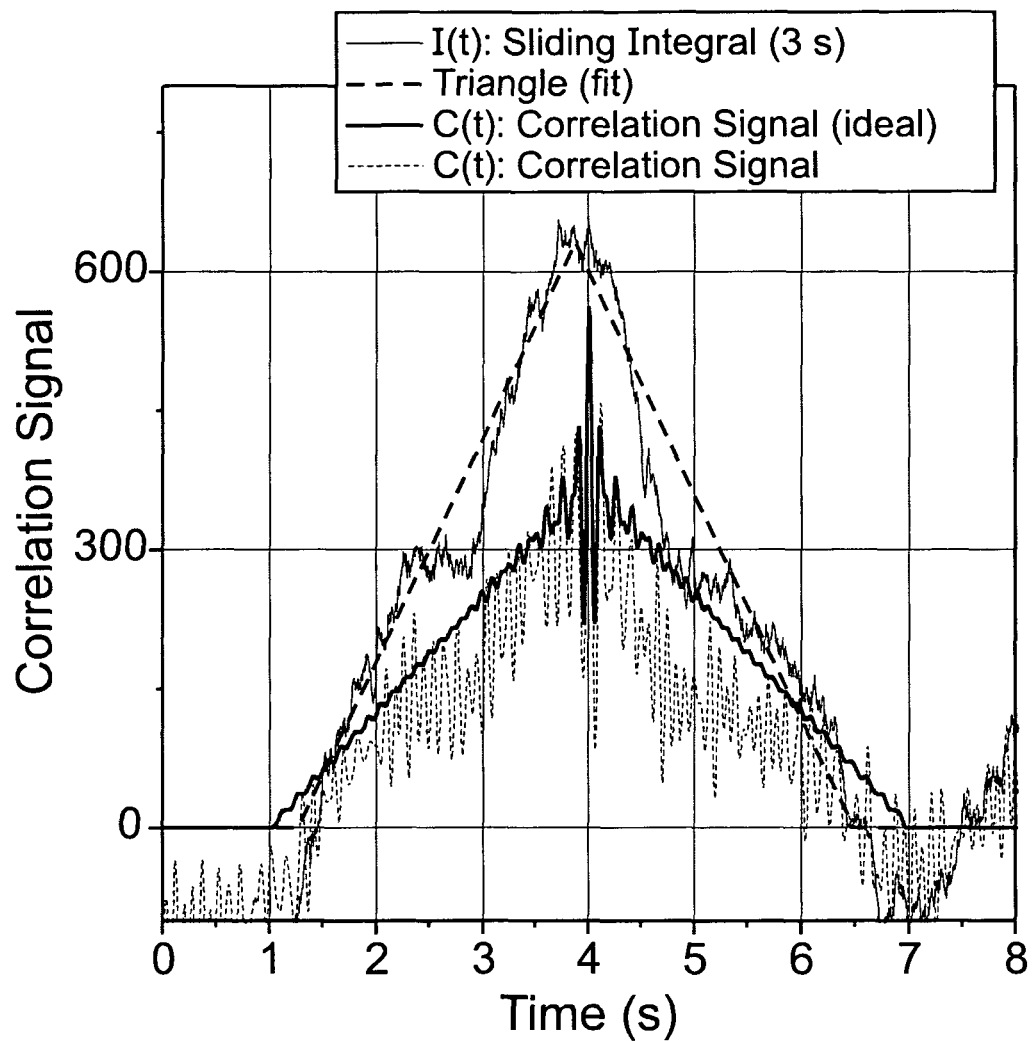
FIG. 10 is a signal used in connection with the presently described embodiments.

With reference now to FIG. 10, a sliding integral is calculated to determine the existence and estimated position of a particle. The sliding integral sums the measured signal S(t) over a defined time period T (e.g. 3 seconds). This calculation is accomplished using the following:

$$I(t) = \int_{t-\tau}^{t} S(\tau) d\tau$$

Once the sliding integral reaches a predetermined threshold, a particle is detected and the positioning algorithm is triggered. This positioning algorithm includes routines that will fit a triangle to the sliding integral. Fitting the triangle allows for determining a rough estimate of the particle position. To more accurately determine the position, a correlation signal is then calculated using the following:

$$C(t) = \int_{t-\tau}^{t} S(\tau) P(\tau - 1 + T) d\tau$$

where,

S(τ) measured signal.

P(τ) is a test signal which is identical to the expected signal which, in this example, is the chirped signal as described above; and T is the length of the chirped test signal P(τ)

Figure 11:
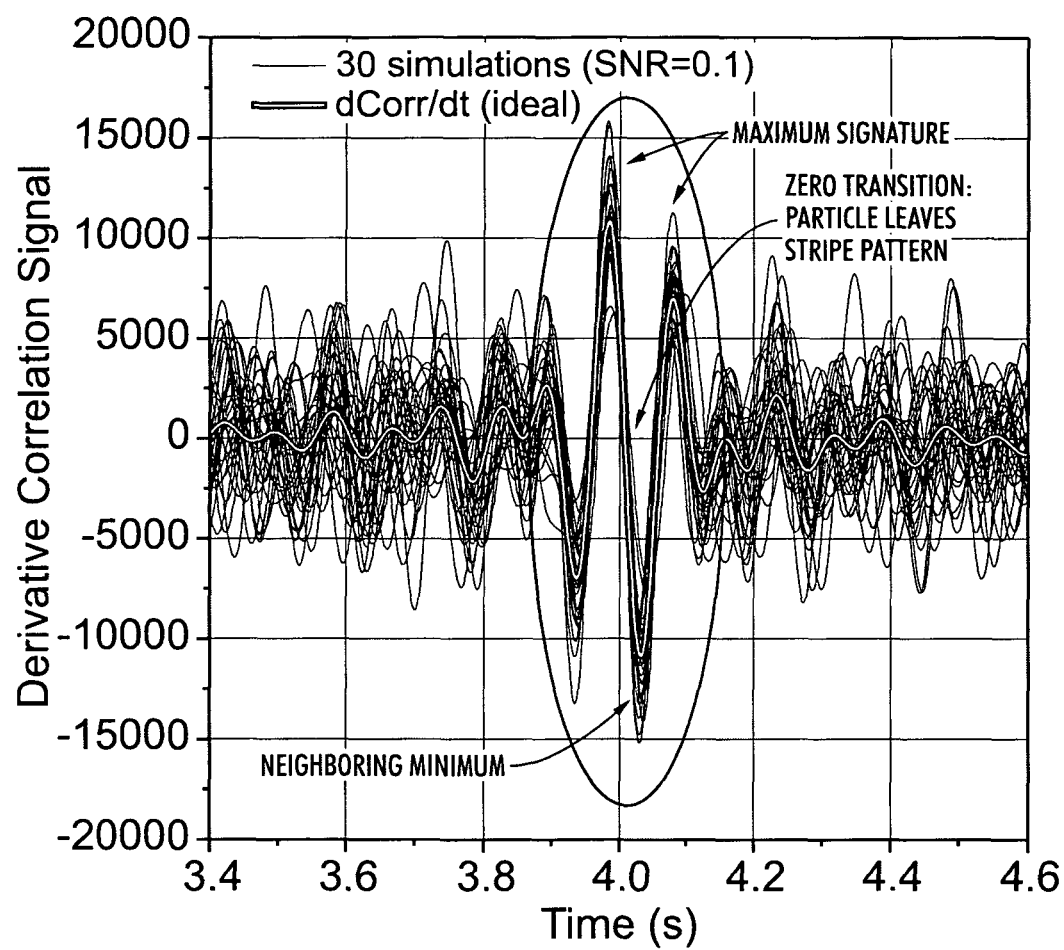
FIG. 11 is a signal used in connection with the presently described embodiments.

FIG. 11 illustrates that the derivative of the correlation signal is then taken. Note that 30 simulations are illustrated as opposed to a single measured and single ideal correlation signal, as in FIG. 10. From the derivative signal, the maximum and minimum in the proximity (e.g. +/−0.5 seconds) of the estimate of the particle position are determined. The maximum difference between the maximum and minimum for all pairs of neighboring maxima and minima is then determined (in this example, one has to compare a maximum and its neighboring minimum to the right). The particle position can then be determined based on the zero transition of the determined maximum difference (zero transition method). In this regard, translation from the zero transition to a position is accomplished as a function of the flow speed of the fluid in the channel. In cases where the fluid is not flowing, the speed of the detector or the microscopic slide, for example, is used to translate the zero transition point to a position.

Figure 12:
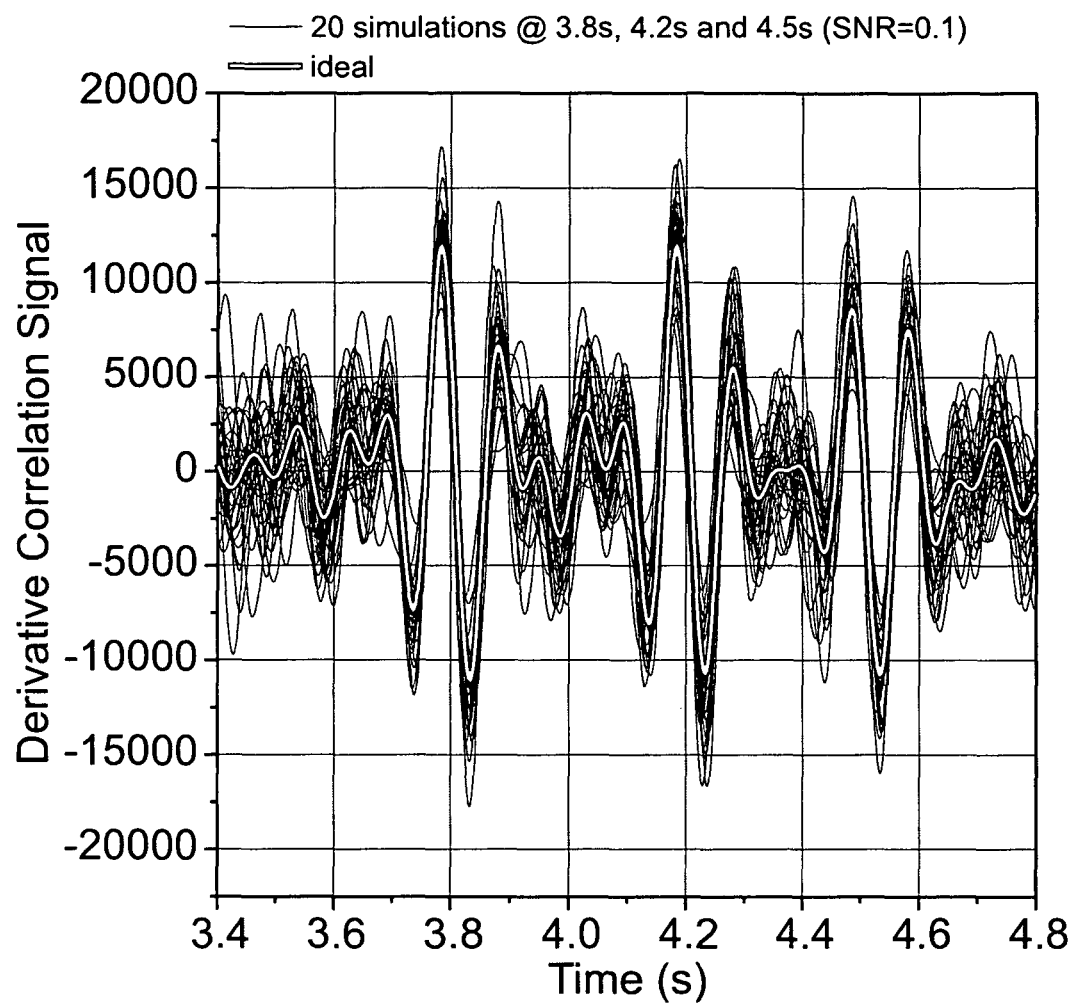
FIG. 12 is a signal used in connection with the presently described embodiments.

The above technique is applied in one form to determine the position of a single particle. However, there is also a need to be able to determine the positions of multiple particles, e.g. two particles. In this case, with reference to FIG. 12, the number of particles within a sliding integral window is evaluated. To do so, the slope of the triangle sides or flanks are measured or the triangle is integrated. The signatures of each particle may be located within the window as described above (zero transition method) in connection with determining the maximum distance between maximums and minimums in the proximity of the estimated position. However, for two particles, the two largest differences (as opposed to only the largest difference) are considered. Again, the signatures are determined relative to the estimated position (e.g. by fitting a calculated ideal signature to the measured signal). Otherwise, the method is the same as above.

Of course, it will be appreciated that this method for determining the position of multiple particles is not effective if the particles are too close together. For the case of the linearly chirped signal in the above mentioned case, a signature width can be defined as (fmax+fmin)/2 fmax fmin, where fmin and fmax are the minimum and maximum frequencies and the frequency of the signal linearly rises from fmin to fmax over the length of the chirped signal. In this regard, if the number of detected particle signatures is smaller than the number of expected particles (as determined by the evaluation techniques above), then it is presumed that at least some of the particles are too close together to be evaluated individually by the zero transition method. Under these circumstances, the ideal correlation signal for two particles is calculated and fitted to the measured correlation signal using particle distance and position of one particle as fit parameter. To obtain reliable fit results, it may be favorable to constrain the parameter particle distance to the signature width.

Figure 13:
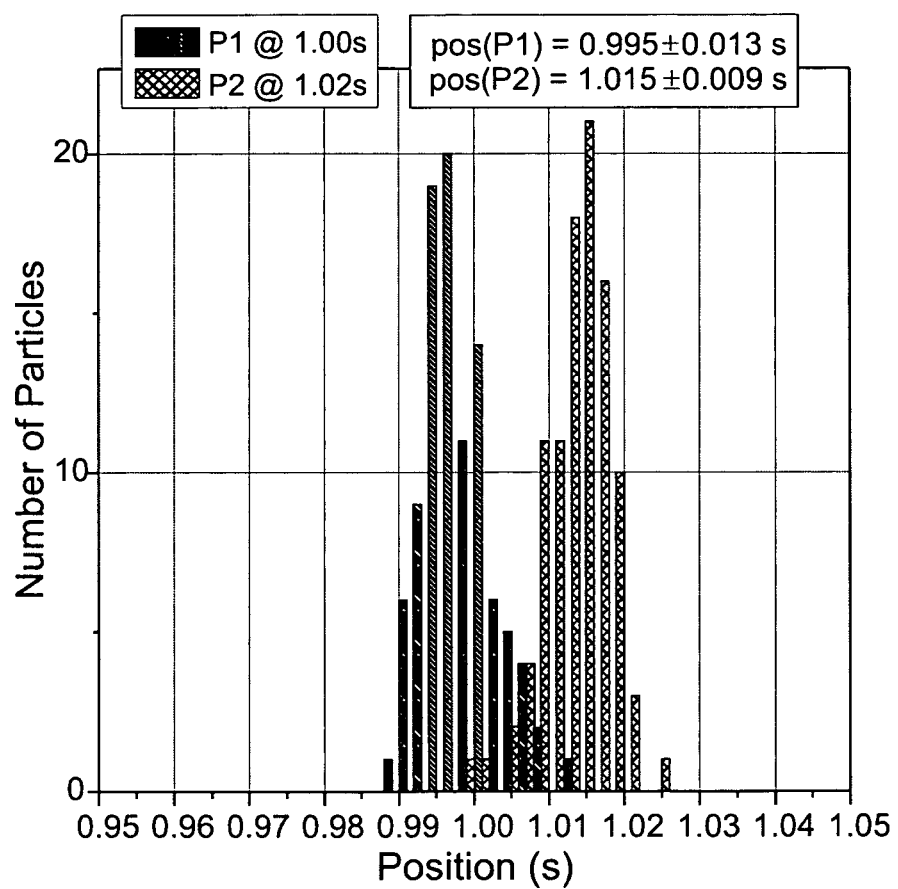
FIG. 13 is a signal used in connection with the presently described embodiments.

With reference now to FIG. 13, simulation results for 100 runs are illustrated. In this simulation, Particle 1 (P1) and Particle 2 (P2) have a distance of 0.02 s where the signature width is 0.11. A low signal to noise ratio of SNR=0.1 is assumed. So, the particles can be distinguished and the position of both particles can be measured by an accuracy of better than 1/5 of the signature width.

Figure 14:
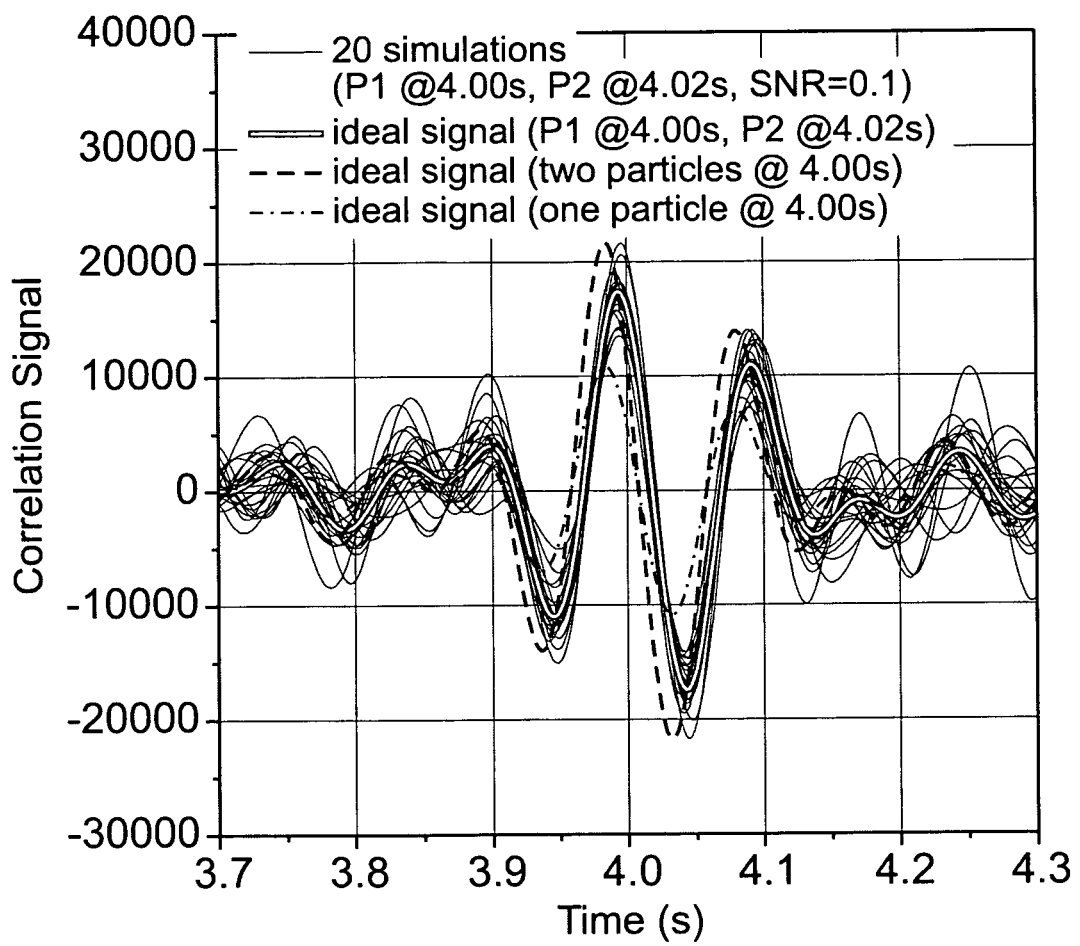
FIG. 14 is a signal used in connection with the presently described embodiments; and, FIG. 15 is an illustration of types of signals that may be analyzed in connection with the presently described embodiments.

Further, referring now to FIG. 14, the overlapping nature of the signature of close particles is illustrated. It can be seen that only one zero transition occurs for the overlapping signal which is composed of the signal of two particles close together. Nevertheless, the particular shape of the overlapping signal is sufficiently different from the case of a single particle and the case of two particles at the same position to be reliably identified. To find the position of each particle, the ideal curve is fitted to the measurement. The parameters of the fit are the positions of each particle.

Further variations of the presently described embodiments are contemplated. As mentioned above, several test functions and fitting functions can be applied.

In addition, in the case of low noise, it might be favorable to skip the correlation enhancement step and fit the signal directly with an appropriate fitting function (e.g., sinusoid).

Fourier-Transformation techniques can be used to determine the frequency and phase of the modulated signals.

In accord with the presently described embodiments, relative motion between the particle and the spatially modulated excitation or emission pattern is described. However, instead of moving the particle through the spatially modulated excitation pattern, the detection system can also be scanned along a channel or carrier/chip. In the case of a chip the particles of interest are fixed on the chip and, e.g., the absolute position of particles on the chip is determined.

The concept can, for example, also be applied to fluorescence read-out of a bio-chip.

Spatial modulations can be achieved in different manners. For example, geometry may provide a basis for spatial modulation. In this regard, a spatially modulated shadow mask, e.g. interdigitated finger-type mask, a spatially modulated phase mask, a micro-lens array or a micro-mirror array may be used.

Spatial modulation may also be achieved using electric or magnetic fields. In this regard, emitted fluorescence intensity can be affected by the modulated field. Also, the density of the fluorescence object may be modulated by the field and the optical path can be affected by the field.

Spatially modulated acoustic field (standing or moving acoustic waves, surface acoustic waves) may also be used. In this regard, emitted fluorescence intensity can be impacted by the modulated field. The density of the fluorescence object may be modulated by the field. And, the optical path can be affected by the field.

Spatially modulated environment (e.g. stationary molecular coatings) within the moving path creating a spatially modulated fluorescence quenching may also be useful.

A spatially modulated micro-cavity which influences the emission properties of the moving object may likewise be applied to achieve objectives of the presently described embodiments.

The signal processing can either be completely software based as described above or partly done by electronic circuitry. In this regard, it should be understood that the presently described embodiments may be implemented using a variety of different hardware configurations and/or software techniques. The precise implementation may depend on the ultimate application of the presently described embodiments. For example, the presently described embodiments may be implemented as one or a series of software routines that reside on a detector system in a bio-medical system used by a hospital. Or, the routines and techniques of the presently described embodiments may be distributed among a variety of laboratory tools used in an experimental environment. As noted above, in at least one form, the techniques of the presently described embodiments are implemented using a suitable processing module that is capable of processing the data contemplated herein (such as processing module 21 of FIG. 1 or other such modules).

The technique can be also applied to data analysis of the fluorescence signal of biochips in order to receive high spatial resolution and high sensitivity.

Further, as previously noted, the techniques described herein may be used in two-dimensional analysis of particles. A system for accomplishing this is described in U.S. Method and System Implementing Spatially Modulated Excitation or Emission for Particle Publication No. 2008/0181827 filed of even date herewith, is incorporated herein by reference.

Moreover, the presently described embodiments have been described in terms of optical or light signals. It will be appreciated that the presently described embodiments may be extended to non-optical signals. For example, capacitance, inductance or resistance could be used to generate a signal to implement the teachings herein.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of operating a particle analyzer for determining a position of a particle, the method comprising:
    detecting, in a detector of the particle analyzer, energy modulated by relative motion between the particle and a spatially modulated pattern including at least three first features that alternate positionally with at least three second features;
    recording a time modulated signal that corresponds to the modulation of the energy, the time modulated signal including more than three transitions from an on state to an off state;
    determining, by a processor of the particle analyzer, the position of the particle, comprising:
        applying a correlation routine by correlating the time modulated signal to a test signal to generate a correlation signal;
        applying a fit function to the correlation signal; and,
        extracting the position of the particle based on the applying of the fit function.

2. The method as set forth in claim 1 wherein two positions are detected in order to calculate the distance between both positions.

3. The method as set forth in claim 1 wherein the particle is a DNA sequencing tag and the detecting is based on an optical bar code read out.

4. The method as set forth in claim 1 wherein the particle is disposed on a bio-chip.

5. The method as set forth in claim 1 wherein the fit function is a triangle.

6. The method of claim 1, wherein detecting the particle comprises detecting based on relative motion between the particle and a spatially modulated excitation pattern.

7. The method of claim 1, wherein detecting the particle is achieved using at least one of a spatially modulated shadow mask, a spatially modulated phase mask, a micro-lens array, or a micro-mirror array.

8. The method of claim 1, wherein detecting the particle is achieved using at least one of a spatially modulated electrode array, spatially modulated magnetic field sensors, spatially modulated acoustic field sensors, or spatially modulated micro-cavities.

9. The method of claim 1, wherein detecting the particle is achieved using spatially modulated fluorescence quenching.

10. The method of claim 1, wherein the test function is a sinusoid with a periodicity of the recorded signal frequency.

11. The method of claim 1, wherein applying the fit function comprises independently varying a position of the fit function e to the time modulated signal.

12. The method of claim 1, wherein:
    applying the fit function comprises applying multiple fit functions and independently varying a position of each of the multiple fit functions relative to the time modulated signal; and
    determining the position of the particle comprises:
        determining a position of a first particle; and
        determining a position of a second particle.

13. The method of claim 1, wherein the test signal is an expected time modulated signal.

14. The method of claim 1, wherein determining the position of the particle comprises determining the position relative to an environment of the particle that includes the spatially modulated pattern or to a position of another particle.

15. A method of operating a particle analyzer to determine a position of at least one particle comprising:
- detecting in a detector of the particle analyzer energy modulated by relative motion between the particle and a spatially modulated pattern including at least three first features that alternate positionally with at least three second features;
- recording a time modulated signal that corresponds to the modulation of the energy, the time modulated signal including more than three transitions from an on state to an off state;
- determining, in a processor of the particle analyzer, the position of the particle, comprising:
  - calculating a sliding integral over time on the time modulated signal;
  - applying a fit function to the sliding integral to obtain an estimated position of the particle;
  - calculating a correlation signal to eliminate noise;
  - calculating a derivative signal of the correlation signal;
  - determining a maximum and a minimum of the derivative signal based on the estimated position of the particle;
  - determining a zero transition of the derivative signal; and
  - determining a position of the particle based on the zero transition of the derivative signal.

16. The method as set forth in claim 15 wherein the fit function is a triangle.

17. The method as set forth in claim 16 further comprising determining the slope of flanks of the triangle to determine if multiple particles are present.

18. The method as set forth in claim 16 further comprising integrating the triangle to determine if multiple particles are present.

19. The method as set forth in claim 15 wherein the determining the maximum and the minimum comprises determining multiple maximums and minimums to determine the positions of multiple particles.

20. The method as set forth in claim 15 wherein the method is applied in two dimensions to determine a location of the particle.

21. The method as set forth in claim 15 further comprising the use of least squares fitting of a measured signal to determine the positions of multiple particles that are within a predetermined distance from one another.

22. The method as set forth in claim 15 wherein the energy is optical energy and the time modulated signal corresponds to modulated optical energy.

23. The method as set forth in claim 22 whereby the optical energy is light.

24. The method as set forth in claim 15 wherein:
the energy is non-optical energy the time modulated signal corresponds to modulated non-optical energy.

25. The method as set forth in claim 15 wherein the correlation signal is based on a chirp signal.

26. The method as set forth in claim 15 wherein the time modulated signal is periodic.

27. The method as set forth in claim 15 wherein the time modulated signal is based on a known signal.

28. A particle analyzer system for determining a position of a particle comprising:
- a spatially modulated pattern including at least three first features alternating positionally with at least three second features;
- a detector configured to detect energy modulated by relative motion between the particle and the spatially modulated pattern and:
  - to record a time modulated signal that corresponds to the modulation of the energy; and
- a processor configured to:
  - apply a correlation routine to correlate the time modulated signal to a test signal to generate a correlation signal,
  - apply a fit function to the correlation signal, and
  - extract the position of the particle based on applying of the fit function.

29. The system as set forth in claim 28 wherein the particle is a DNA sequencing tag.

30. The system as set forth in claim 28 wherein the particle is disposed on a bio-chip.

31. The system as set forth in claim 28 wherein the fit function is a triangle.

32. A particle analyzer system to determine a position of at least one particle comprising:
- a spatially modulated pattern including at least three first features alternating positionally with at least three second features;
- a detector configured to detect energy modulated by relative motion between the particle and the spatially modulated pattern and
- a to record a time modulated signal that corresponds to modulation of the energy, the time modulated signal including more than three transitions from an on state to an off state; and
- a processor configured to calculate a sliding integral over time on the recorded signal, to apply a fit function to the sliding integral to obtain an estimated position of the particle, to calculate a correlation signal, to calculate a derivative signal of the correlation signal, to determine a maximum and a minimum of the derivative signal based on the estimated position of the particle, to determine a zero transition of the derivative signal, and to determine a calculated position of the particle based on the zero transition of the derivative signal.

* * * * *